United States Patent [19]

Chadwick et al.

[11] Patent Number: 5,292,912

[45] Date of Patent: Mar. 8, 1994

[54] CATALYTIC CONVERSION OF DIRECT PROCESS HIGH-BOILING COMPONENT TO CHLOROSILANE MONOMERS IN THE PRESENCE OF HYDROGEN CHLORIDE

[75] Inventors: Kirk M. Chadwick, S. Glamorgan, Wales; Ajay K. Dhaul, Carrollton, Ky.; Roland L. Halm, Madison; Richard G. Johnson, Hanover, both of Ind.

[73] Assignee: Dow Corning Corporation, Midland, Mich.

[21] Appl. No.: 94,593

[22] Filed: Jul. 19, 1993

[51] Int. Cl.$^5$ .............................................. C07F 7/08
[52] U.S. Cl. ........................................ 556/468; 556/466
[58] Field of Search ............................... 556/468, 466

[56] References Cited

U.S. PATENT DOCUMENTS

| | | | |
|---|---|---|---|
| 2,380,995 | 8/1945 | Rochow | 556/472 |
| 2,488,487 | 11/1949 | Barry et al. | 556/472 |
| 2,598,435 | 5/1952 | Mohler et al. | 556/468 |
| 2,681,355 | 6/1954 | Barry et al. | 556/468 |
| 2,709,176 | 5/1955 | Bluestein | 556/468 |
| 2,787,627 | 4/1957 | Kuriyagawa et al. | 556/468 |
| 2,842,580 | 7/1958 | Gilbert | 556/468 |
| 3,006,943 | 10/1961 | Nitzsche et al. | 556/468 |
| 3,432,537 | 3/1969 | Guinet et al. | 556/468 |
| 3,639,105 | 2/1972 | Atwell et al. | 556/468 |
| 4,059,608 | 11/1977 | Calas et al. | 556/468 |
| 4,079,071 | 3/1978 | Neale | 556/468 |
| 4,461,908 | 7/1984 | Takamizawa et al. | 556/468 X |
| 4,578,495 | 3/1986 | Soula et al. | 556/468 |
| 4,958,040 | 9/1990 | Yoshioka et al. | 556/468 X |
| 5,210,255 | 5/1993 | Kalchauer et al. | 556/468 |

*Primary Examiner*—Paul F. Shaver
*Attorney, Agent, or Firm*—William F. Boley

[57] ABSTRACT

The present invention is a process for converting a high-boiling component resulting from the reaction of an organochloride with silicon into commercially more desirable monosilanes. The process comprises contacting the high-boiling component with hydrogen chloride at a temperature within a range of about 250° C. to 1000° C. in the presence of a catalyst selected from a group consisting of activated carbon, platinum supported on alumina, zeolite, AlCl$_3$, and AlCl$_3$ supported on a support selected from a group consisting of carbon, alumina, and silica.

15 Claims, No Drawings

CATALYTIC CONVERSION OF DIRECT PROCESS HIGH-BOILING COMPONENT TO CHLOROSILANE MONOMERS IN THE PRESENCE OF HYDROGEN CHLORIDE

BACKGROUND OF INVENTION

The present invention is a process for converting a high-boiling component resulting from the reaction of an organochloride with silicon into commercially more desirable monosilanes. The process comprises contacting the high-boiling component with hydrogen chloride at a temperature within a range of about 250° C. to 1000° C. in the presence of a catalyst selected from a group consisting of activated carbon, platinum supported on alumina, zeolite, $AlCl_3$, and $AlCl_3$ supported on a support selected from a group consisting of carbon, alumina and silica.

The high-boiling component useful in the present process results from a process typically referred to as the "Direct Process," where an organohalide is reacted with silicon metalloid in the presence of a suitable catalyst to form monosilanes. The Direct Process as described by, for example, Rochow, U.S. Pat. No. 2,380,995, issued Aug. 7, 1945, and Barry et al., U.S. Pat. No. 2,488,487, issued Nov. 15, 1949, is the main commercial process by which organohalosilanes (i.e. monosilanes), for example, dimethyldichlorosilane and trimethylchlorosilane are formed. These organohalosilanes are reactive compounds which can undergo numerous reactions to form a variety of useful silicon containing compounds and polymers. A major commercial use of organohalosilanes is in the production of polysiloxane polymers which are useful as heat transfer fluids, lubricants, and the like and which can be further processed, for example, to form silicone elastomers, resins, sealants, and adhesives.

Operation of the Direct Process results not only in the production of the desirable monosilanes, but also in a high boiling component typically considered to be all materials with a boiling point higher than the particular diorganodihalosilane produced in the process. The high-boiling component is a complex mixture that includes compounds containing SiSi, SiOSi, SiCSi, SiCCSi, and SiCCCSi linkages in the molecules. Some typical compounds are described, for example, in Mohler et al., U.S. Pat. No. 2,598,435, issued May 27, 1952, and Barry et al., U.S. Pat. No. 2,681,355, issued Jun. 15, 1954. The high-boiling component may also comprise silicon containing solids and soluble and insoluble compounds of copper, aluminum, and zinc.

In current commercial operations for performing the Direct Process, the high-boiling component can constitute as much as ten percent of the resultant product. Therefore, it is desirable to convert the high-boiling component into commercially desirable products to both reduce low-value byproducts and to improve raw material utilization.

Mohler, U.S. Pat. No. 2,598,435, issued May 27, 1952, describes a process for converting methylpolysilanes present in a Direct Process residue to monosilanes, the process comprises heating the residue at a temperature above 250° C. and below the decomposition point of the formed monosilanes.

Barry, U.S. Pat. No. 2,681,355, issued Jun. 15. 1954, observed that the process taught in Mohler, U.S. Pat. No. 2,598,435, can result in significant coking of the reactor making the process unsuitable for commercial cracking processes. Barry, supra, teaches that this coking can be reduced if the Direct Process residue is contacted with at least four percent by weight hydrogen chloride at a temperature from 200° C. to 900° C. Barry also suggests that the process can be run in a reactor packed with either an inert material such as quartz or a catalytic material such as activated alumina or silica alumina.

Bluestein, U.S. Pat. No. 2,709,176, issued May 25, 1955, reports a process for converting the polysilanes present in a Direct Process residue into monosilanes by the use of a tertiary organic amine catalyst. Bluestein reports that when the Direct Process residue is contacted with a hydrogen halide and a tertiary organic amine catalyst, the process can be conducted at temperatures of about 75° C. to 150° C. with acceptable yields of monosilanes being obtained.

Gilbert. U.S. Pat. No. 2,842,580, issued Jul. 8, 1958, reports a process for converting the polysilanes present in a Direct Process residue into monosilanes by the use of quaternary ammonium halide and quaternary phosphonium halide compounds as catalysts. The process of Gilbert is run in the absence of hydrogen chloride. as described by Bluestein supra, and is reported to provide monosilanes with reduced levels of hydrogen bonded to the silicon atoms.

A first objective of the present process is to provide a catalyzed process for the high conversion of a high-boiling component produced by the Direct Process to monosilanes. A second objective is to provide a catalyzed process employing readily available and inexpensive catalysts which can be easily retained in a reactor and which have a long life in the process.

SUMMARY OF INVENTION

The present invention is a process for converting a high-boiling component resulting from the reaction of an organochloride with silicon into commercially more desirable monosilanes. The process comprises contacting the high-boiling component with hydrogen chloride at a temperature within a range of about 250° C. to 1000° C. in the presence of a catalyst selected from a group consisting of activated carbon, platinum supported on alumina, zeolite, $AlCl_3$, and $AlCl_3$ supported on a support selected from a group consisting of carbon, alumina, and silica.

DESCRIPTION OF INVENTION

The present invention is a process for converting a high-boiling component resulting from the reaction of an organochloride with silicon metalloid (hereafter referred to as silicon) to monosilanes. The process comprises contacting a high-boiling component. resulting from the reaction of an organochloride with silicon, and hydrogen chloride at a temperature within a range of about 250° C. to 1000° C. in the presence of a catalyst selected from a group consisting of activated carbon, platinum supported on alumina, zeolite, $AlCl_3$, and $AlCl_3$ supported on a support selected from a group consisting of carbon, alumina, and silica.

The present process may be run in any standard type reactor for contacting silanes and hydrogen chloride. The process may be run as a batch process, semi-continuous. or continuous process. The process can be run, for example, in a fixed-bed reactor, a stirred-bed reactor, or a fluidized-bed reactor. Preferred is when the process is run as a continuous process in a fluidized-bed reactor.

The present process is useful for converting a high-boiling component resulting from the reaction of an organochloride with silicon to form monosilanes. The term "high-boiling component" refers to those materials with a boiling point above that of the diorganodichlorosilane formed by the reaction of the organochloride with silicon. For example when methyl chloride is reacted with silicon, the diorganodichlorosilane will be dimethyldichlorosilane and the high-boiling component will comprise those materials having a boiling point greater than that of dimethyldichlorosilane, i.e. greater than about 70° C.

In a typical process for reacting an organochloride with silicon, the process is conducted at a temperature of about 270° C. to 350° C. in the presence of a suitable catalyst, and gaseous product and unreacted feed are continuously removed from the process. The removed gaseous product and unreacted feed are subsequently distilled to remove monosilanes leaving a high-boiling component.

The high-boiling component is a complex mixture that can include compounds containing SiSi, SiOSi, SiCSi, SiCCSi, and SiCCCSi linkages alone or in combination in each molecule. The high-boiling component can include silicon containing solids and soluble and insoluble compounds of copper, aluminum, and zinc. The high-boiling component may contain, for example, organic substituted and non-organic substituted silanes, disilanes, trisilanes, disiloxanes, silane oligomers, siloxane oligomers, silalkylenes and silicon containing solids, all of which may be converted to monosilanes by the present process.

The present process is useful for converting polysilanes in the high-boiling component to monosilanes, where the polysilanes are described by formula $R_aH_b\text{-}Si_nCl_{n+2-a-b}$ and where each R is a radical independently selected from a group consisting of alkyls comprising one to six carbon atoms, $n=2$ to 20, $a=0$ to $2n+2$, $b=0$ to $2n+2$, and $a+b=0$ to $2n+2$.

The polysilanes useful in the present process can consist of n number of silicon atoms where n is an integer from two to 20. Preferred is when n equals two. The polysilanes can be substituted with $a=0$ to $2n+2$ number of R radicals, where each R is independently selected from a group consisting of alkyls of one to six carbon atoms. The radical R can be, for example, methyl, ethyl, propyl, and t-butyl. Preferred is when R is methyl.

The polysilanes in the high-boiling component can contain b number of hydrogen atoms substituted on the silicon atoms, where $b=0$ to $2n+2$.

The polysilanes in the high-boiling component can contain from zero to $2n+2$ chlorine atoms.

The high-boiling component can contain silalkylenes, where each silalkylene can comprise one or more silalkylene bonds described by formula $Si(C)_zSi$ and z is an integer from one to six. Preferred is when z is an integer from one to three. The silalkylene molecules can comprise SiSi bonds and SiOSi bonds as well as silalkylene bonds. The silicon atoms of the silalkylene molecules can be further substituted with the radical R, where R is as previously described, with chlorine, and with hydrogen. Preferred is when the silicon atoms of the silalkylenes are substituted with methyl.

The preferred high-boiling component is one resulting from the reaction of methyl chloride with silicon, the high-boiling component having a boiling point greater than about 70° C. This high-boiling component can contain, for example, $Me_2ClSiSiMe_2Cl$, $Me_2ClSiSiMeCl_2$, $MeCl_2SiSiMeCl_2$, $Me_2ClSiSi(Me)(Cl)SiMeCl_2$, $Me_2ClSiCH_2SiMe_2Cl$, $Me_2ClSiCH_2SiMeCl_2$, $MeCl_2SiCH_2SiMeCl_2$, $Me_2ClSi(CH_2)_2SiMeCl_2$, $Me_2ClSi(CH_2)_3SiMeCl_2$, $Me_2ClSi(Me)(Cl)SiMeCl_2$, $Me_2ClSiCH_2Si(Me)(Cl)CH_2SiMeCl_2$, and $Me_2ClSiOSiMeCl_2$, where Me is methyl, all of which may be converted to monosilanes by the present process.

The high-boiling component is contacted with hydrogen chloride, where the ratio of the weight of high-boiling component added to the reactor to the weight of hydrogen chloride added to the reactor is within a range of about 5:1 to 0.05:1. Preferred is where the ratio of the weight of high-boiling component to the weight of hydrogen chloride is within a range of about 3:1 to 1:1.

The process is conducted at a temperature within a range of about 250° C. to 1000° C. A preferred temperature is within a range of about 450° C. to 550° C.

While pressure is not critical to the present process, it is preferred that the process be run at a pressure within a range of about zero psig to 1000 psig. More preferred is when the process is run at a pressure within a range of about zero psig to 100 psig.

The process is conducted in the presence of a catalyst selected from a group consisting of activated carbon, platinum supported on alumina, zeolite, $AlCl_3$, and $AlCl_3$ supported on a support selected from a group consisting of carbon, alumina, and silica.

A preferred catalyst is activated carbon. By "activated carbon" it is meant a microcrystalline. nongraphite form of carbon, having an internal porosity, the carbon having been activated by any standard process known in the art for producing activated carbon, for example, chemical activation or gas activation as described in Kirk-Othmer, Concise Encyclopedia of Chemical Technology, John Wiley & Sons publishers. 1985, p. 204 to 205. The activated carbon can be in the form of, for example, flakes, chips, particles, powder, or pellets.

In general, it is preferred that the activated carbon have a diameter within a range of about 0.001 mm to 20 mm. More preferred is when the activated carbon has a diameter within a range of about 0.01 mm to 5 mm and a surface area greater than about 1000 m²/g.

The weight of activated carbon in relation to the weight of high-boiling component and hydrogen chloride added to the process will depend upon such factors as the type and size of the activated carbon, the chemical composition of the high-boiling component, the process temperature, and the type of reactor employed. When the process is run as a batch process or a semi-continuous process a useful weight of activated carbon is considered to be within a range of about 0.1 to 30 weight percent of the combined weight of the high-boiling component and the hydrogen chloride added to the process.

The catalyst can be platinum supported on alumina. The amount of platinum supported on alumina can be from about 0.1 to 10 weight percent platinum. Preferred is when the amount of platinum supported on alumina is within a range of about 0.5 to 2.0 weight percent platinum. The concentration of platinum supported on alumina catalyst used in the process will depend upon such factors as discussed for the use of activated carbon. In general, when the process is run as a batch process or semi-continuous process a useful concentration of platinum on alumina catalyst is considered to be that which provides a catalyst concentration within a range of about 0.1 to 30 weight percent of the combined weight of the high-boiling component and the halogen chloride added to the process.

The catalyst can be a zeolite. The zeolite catalyst can be of the natural occurring type, for example, chabazite, mordenite, erionite, faujasite, and clinoptilolite. The zeolite catalyst can be a synthetic zeolite, for example, of the zeolite A, X, L, or Y types or of the high silica synthetic zeolite types such as ZSM-5 and ZSM-11. Preferred is when the zeolite catalyst is selected from a group of synthetic zeolite catalyst consisting of LZ-Y-64, LZ-Y-74, and LZ-M-8.

The concentration of zeolite catalyst used in the process will depend upon such factors as discussed for the use of activated carbon. In general, when the process is run as a batch process or semi-continuous process a useful concentration of zeolite is considered to be within a range of about 0.1 to 30 weight percent of the combined weight of the high-boiling component and the hydrogen chloride added to the process.

The catalyst can be $AlCl_3$. The concentration of $AlCl_3$ catalyst used in the process will depend upon such factors as discussed for the use of activated carbon. In general, when the process is run as a batch process or semi-continuous process a useful concentration of $AlCl_3$ catalyst is considered to be within a range of about 0.1 to 30 weight percent of the combined weight of the high-boiling components and the hydrogen chloride added to the process.

The catalyst can be $AlCl_3$ supported on a support selected from a group consisting of carbon, alumina, and silica. The amount of $AlCl_3$ supported on the support can within a range of about 0.1 to 20 weight percent. Preferred is when the amount of $AlCl_3$ supported on the support is within a range of about 0.5 to 5.0 weight percent. The concentration of supported $AlCl_3$ used in the process will depend upon such factors as discussed for the use of activated carbon. In general, when the process is run as a batch process or a semi-continuous process a useful concentration of supported $AlCl_3$ catalyst is considered to be within a range of about 0.1 to 30 weight percent of the combined weight of the high-boiling component and the hydrogen chloride added to the process.

The optimum contact time for the high-boiling component and hydrogen chloride with the catalyst will depend, for example, on factors such as the type of catalyst, chemical composition of the high-boiling component, and the degree of conversion and product selectivity desired. In general contact times within a range of about one second to five hours are considered useful. Longer contact times may be employed, but appear to offer no advantage and may result in excessive scission of silicon-carbon bonds and silicon-hydrogen bonds present in the monosilanes. A preferred contact time in a continuous reactor system is within a range of about one second to five minutes.

If desired, the monosilane containing product of the present process can be further separated by standard means, for example, distillation to separate the monosilanes from a high-boiling component and the high-boiling component recycled to the process.

The following examples are provided to facilitate understanding and to demonstrate the effectiveness of the present invention. These examples are not intended to limit the scope of the claims provided herein.

EXAMPLE 1

(Not within the scope of the present invention). A high-boiling component resulting from the reaction of methyl chloride with silicon was contacted with hydrogen chloride in the absence of catalyst. The reactor consisted of a 2.5 cm diameter by 50 cm length quartz tube maintained at about 500° C. The high-boiling component consisted of, by weight, 55% methylchlorodisilane. 5% disilmethylenes, 35% other polysilanes and silalkylenes, and 5% silicon containing solids. The high-boiling component was fed at a rate of 117 g/h to the reactor and hydrogen chloride was fed to the reactor at 50 g/h. The process was conducted for one hour with gaseous product exiting the reactor being collected in a cold condenser. The condensed product was analyzed by gas chromatography using a thermal conductivity detector (GC-TC) and found to consist of 59 weight percent chlorosilane monomers. Chlorosilane monomers detected included $HSiCl_3$, $SiCl_4$, $MeHSiCl_2$, $Me_3SiCl$, $MeSiCl_3$, and $Me_2SiCl_2$. Other species detected in the condensed product included methylchlorodisilanes, disilmethylenes, polysilanes and silalkylenes.

EXAMPLE 2

A high-boiling component resulting from the reaction of methyl chloride with silicon was contacted with hydrogen chloride in the presence of a packed bed of activated carbon catalyst. The process was conducted similar to that described in Example 1, with the high-boiling component composition, reactor design, and reaction temperature being the same. The reactor was packed with 12 g of Calgon BPL 1 mm by 3.3 mm activated carbon pellets (Calgon, Pittsburgh, Pa.). The high-boiling component was fed to the reactor at a rate of 92 g/h and hydrogen chloride was fed to the reactor at a rate of 57 g/h. Gaseous product exiting the reactor was collected and analyzed as described in Example 1. The collected product was found to comprise 93 weight percent chlorosilane monomers and included those chlorosilane monomers described for the product of Example 1.

EXAMPLE 3

A high-boiling component resulting from the reaction of methyl chloride with silicon was contacted with hydrogen chloride in the presence of activated carbon catalyst in a fluidized-bed reactor. The composition of the high-boiling component, reactor design, and process temperature was similar to that described in Example 1. The reactor was filled with 25 g of a 0.1 mm to 0.3 mm pulverized activated carbon (North American, Columbus, Ohio). The high-boiling component was fed to the reactor at a rate of 75 g/h and hydrogen chloride was fed to the reactor at a rate of 57 g/h. The process was conducted for 24 hours with gaseous product exiting the reactor being collected and analyzed as described in Example 1.

The collected product was determined to consist of similar species as identified in Example 1. Of the product collected, 88 weight percent was chlorosilane monomers.

EXAMPLE 4

A high-boiling component resulting from the reaction of methyl chloride with silicon was contacted with hydrogen chloride in the presence of a zeolite catalyst. The process was conducted similar to that described in Example 1, with the high-boiling component composition, reactor design, and reaction temperature being the same. The reactor was packed with 15 g of zeolite LZ-Y-74 extruded 1.6 mm pellets (UOP Inc., Tarrytown, N.Y.). The high-boiling component was fed to the reactor at a rate of 75 g/h and hydrogen chloride was fed to the reactor at a rate of 57 g/h. The process was conducted for one hour with gaseous product exiting the reactor being collected and analyzed as described in Example 1.

The collected product was determined to consist of similar species as described in Example 1. Of the product collected, 81 weight percent was chlorosilane monomers.

EXAMPLE 5

A high-boiling component resulting form the reaction of methyl chloride with silicon was contacted with hydrogen chloride in the presence of a platinum on alumina catalyst. The process was conducted similar to that described in Example 1, with the high-boiling component composition, reactor design, and reaction temperature being the same. The reactor was packed with 16 g of a one weight percent platinum on 1.6 mm alumina spheres (UOP Inc., Tarrytown, N.Y.). The high-boiling component was fed to the reactor at a rate of 88 g/h and hydrogen chloride was fed to the reactor at a rate of 57 g/h. The process was conducted for one hour with gaseous product exiting the reactor being collected and analyzed as described in Example 1.

The collected product was determined to consist of similar species as described in Example 1. Of the product collected, 82 weight percent was chlorosilane monomers.

We claim:

1. A process for converting a high-boiling component resulting from the reaction of an organochloride with silicon, to monosilanes, the process comprising: contacting a high-boiling component, resulting from the reaction of an organochloride with silicon, and hydrogen chloride at a temperature within a range of about 250° C. to 1000° C. in the presence of a catalyst selected from a group consisting of activated carbon, platinum supported on alumina, zeolite, $AlCl_3$, and $AlCl_3$ supported on a support selected from a group consisting of carbon, alumina, and silica.

2. A process according to claim 1, where the temperature is within a range of about 450° C. to 550° C.

3. A process according to claim 1, where the process is conducted at a pressure within a range of about zero psig to 100 psig.

4. A process according to claim 1, where the ratio of the weight of the high-boiling component added to the process to the weight of the hydrogen chloride added to the process is within a range of about 5:1 to 0.05:1.

5. A process according to claim 1, where the ratio of the weight of the high-boiling component added to the process to the weight of the hydrogen chloride added to the process is within a range of about 3:1 to 1:1.

6. A process according to claim 1, where the high-boiling component results from the reaction of methyl chloride with silicon.

7. A process according to claim 1, where the high-boiling component comprises polysilanes and silalkylenes.

8. A process according to claim 1, where the high-boiling component comprises polysilanes described by formula $R_aH_bSi_nCl_{2n+2-a-b}$, where each R is a radical independently selected from a group consisting of alkyls comprising one to six carbon atoms, $n=2$ to 20, $a=0$ to $2n+2$, $b=0$ to $2n+2$, and $a+b=0$ to $2n+2$.

9. A process according to claim 1, where the high-boiling component comprises silalkylenes comprising one or more silalkylene bonds described by formula $Si(C)_zSi$ and $z=1, 2$, or 3.

10. A process according to claim 1, where the high-boiling component comprises soluble and insoluble compounds of copper, aluminum, and zinc.

11. A process according to claim 1, where the catalyst is selected from a group consisting of activated carbon, zeolite LZ-Y-74, and platinum supported on alumina.

12. A process according to claim 1, where the catalyst is activated carbon.

13. A process according to claim 1, where the catalyst is activated carbon having a diameter within a range of about 0.01 to 5 mm and a surface area greater than about 1000 $m^2/g$.

14. A process according to claim 1, where the catalyst is activated carbon and the high-boiling component results from the reaction of methyl chloride with silicon and the high-boiling component comprises polysilanes, silalkylenes, silicon containing solids, and soluble and insoluble compounds of copper, aluminum, and zinc.

15. A process according to claim 8, where R is methyl.

* * * * *